United States Patent [19]

Ebdon et al.

[11] 4,287,042
[45] Sep. 1, 1981

[54] ION-SELECTIVE ELECTRODE AND METHOD OF MAKING SAID ELECTRODE

[75] Inventors: Leslie C. Ebdon; Andrew T. Ellis; George C. Corfield, all of Sheffield, England

[73] Assignee: National Research Development, Corp., London, England

[21] Appl. No.: 127,749

[22] Filed: Mar. 6, 1980

[30] Foreign Application Priority Data

Mar. 9, 1979 [GB] United Kingdom ............. 08452/79

[51] Int. Cl.³ ............................................. G01N 27/30
[52] U.S. Cl. ................................ 204/195 M; 204/296
[58] Field of Search ........................... 204/195 M, 296

[56] References Cited

U.S. PATENT DOCUMENTS

| 3,247,133 | 4/1966 | Chen | 204/296 X |
|---|---|---|---|
| 3,691,047 | 9/1972 | Ross et al. | 204/296 X |
| 3,887,499 | 6/1975 | Hodgdon | 204/296 X |
| 3,932,233 | 1/1976 | Ruzicka et al. | 204/195 M |
| 4,115,209 | 9/1978 | Freiser et al. | 204/1 T |
| 4,151,049 | 4/1979 | Janata | 204/1 T |

FOREIGN PATENT DOCUMENTS 2510071 9/1975 Fed. Rep. of Germany .......... 204/296

OTHER PUBLICATIONS

S. G. Cutler et al., J. Electroanal. Chem., 85, 145–161, (1977).
L. Keil et al., Analyst, 102, 274–280, (1977).

Primary Examiner—G. L. Kaplan
Attorney, Agent, or Firm—Oblon, Fisher, Spivak, McClelland & Maier

[57] ABSTRACT

An ion-selective electrode comprises a standard solution of the ion, such as calcium, and, retaining the solution, a membrane including sensor groups. The sensor groups are secured in the membrane by cross-linking. The membrane may be a styrene-butadiene-styrene triblock elastomeric copolymer, with dialkyl phosphate cross-linked sensor groups resulting from a cross-linking reaction between the membrane and diallyl phosphoric acid.

26 Claims, 1 Drawing Figure

U.S. Patent        Sep. 1, 1981        4,287,042
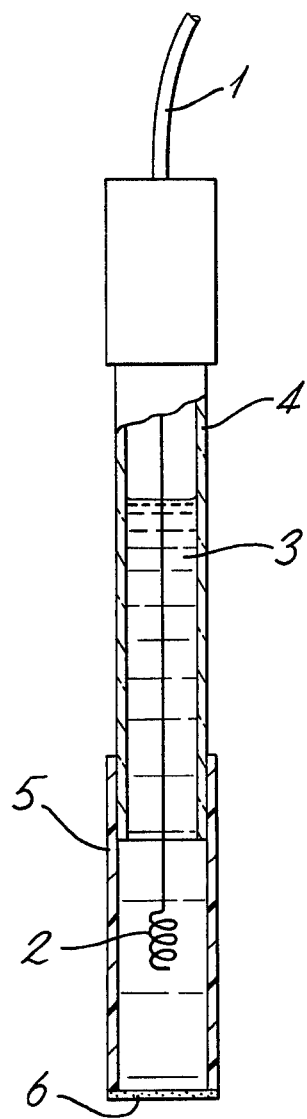

ION-SELECTIVE ELECTRODE AND METHOD OF MAKING SAID ELECTRODE

This invention relates to an ion-selective electrode. Ion-selective electrodes are now sufficiently well established to be generally simple to operate, sensitive and suited to on-line measurement for laboratory analyses, applications to pollution monitoring, in vivo biological measurements and process control. However, known ion-selective electrodes in general lack longevity, adequate selectivity and mechanical strength.

Originally, ion-selective electrodes used glass or crystalline membranes, across which only the selected species of ion could migrate or be exchanged. Later, electrodes based on liquid ion-exchangers were introduced, for example a calcium electrode comprising calcium didecyl phosphate as sensor (ion-exchanger) in conjunction with di(n-octylphenyl)phosphonate solvent-mediator supported on a Millipore filter, marketed e.g. as Orion 92-20. Millipore and Orion are trade marks. In this electrode, three liquids (the internal standard solution, the ion-exchanger and the test solution) must be kept in electrolytic contact but prevented from mixing. Indeed the lifetime of this electrode is limited by leaking, whose onset tends to raise the limit of detection.

This electrode has been modified by incorporating the sensor and the solvent-mediator into a poly(vinylchloride), (PVC), membrane, which in use separates the standard solution from the test solution. The standard solution is standard with respect to the ion to which the electrode is selective, and in use usually contacts a metal/insoluble-salt-of-the-metal electrode; the standard solution and the insoluble salt have a common anion. This construction is convenient and cheap, but still has a limited life-time because the sensor, which transports selectively the ion of interest, can be leached out of the PVC membrane.

A recent attempt to overcome the leaching problem involved immobilising sensors in the membrane by covalent bonding, in particular by phosphorylating a vinyl chloride-vinyl alcohol copolymer with decyl dihydrogen phosphate. The copolymer was then mixed with PVC in which di(n-octylphenyl)phosphate was entangled to produce a calcium-selective electrode. The lifetime of this electrode was about 2 weeks. Another proposal was to bind the sensor groups to the ends of PVC chains both by the use of an amine as chain transfer agent during polymerisation and by the use of the $SO_3{}^-$ radical-anion as polymerisation initiator. The electrode so produced exhibited selectivity to anionic or cationic surfactants and, although having a longer life-time, the plasticizer used (tricresyl phosphate) was leached from the polymer and this still limited electrode life-time.

Thus, a known ion-selective electrode comprises a standard solution of the ion and, retaining the solution, a membrane including sensor groups covalently bonded to it.

According to our invention, at least part of the covalent bonding is by cross-linking. The membrane per se made in this way is believed to be new, and can be regarded as a means relating to an essential element of the invention for putting the invention into effect.

Preferably, the membrane is produced from a polymer (preferably a linear polymer) which had unsaturated bonds which have received the cross-linking. For example, the polymer may be a styrene-butadiene-styrene triblock copolymer. Preferably the membrane displays elastomeric properties.

The sensor group may comprise

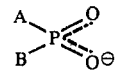

where A and B are moieties cross-linking the polymer, so that the electrode is calcium-selective. The sensor group thus preferably is an organophosphate or an organophosphonate, e.g. dialkyl phosphate (so that the electrode is calcium-selective). The dialkyl phosphate may result directly from a cross-linking reaction of diallyl phosphoric acid with the membrane, usually the above copolymer, or, preferably, it may result indirectly from a cross-linking reaction of, say, triallyl phosphate, tri($\omega$-undecenyl)phosphate or diallyl phenylphosphonate with the copolymer, yielding covalently bound trialkyl phosphate, which reaction may be free-radical initiated, for example by ultraviolet irradiation. This may be followed by hydrolysis converting the trialkyl phosphate to dialkyl phosphate.

The hydrolysis preferably lasts at least 1 hour, more preferably at least 3 hours and most preferably at least 4 hours, and can be up to 20 hours, more suitably up to 10 hours. Aqueous alkali in a concentration of up to 20% by weight may be used, or else, for a milder hydrolysis, up to 8% (preferably 3 to 7%) by weight of alkali (preferably KOH or NaOH) in alcohol (preferably ethanol, more preferably methanol).

The triallyl or tri($\omega$-undecenyl) or other phosphate or the diallyl phenyl or other phosphonate may be present in a proportion of 0.3 to 10% by weight (preferably 4 to 6% by weight) with respect to the membrane, usually styrene-butadiene-styrene. A free-radical initiator may be present for initiating the cross-linking, such as $\alpha,\alpha$-azobisisobutyronitrile, in a preferred proportion of 1 to 5% by weight (suitably 2 to 3% by weight) with respect to the membrane.

Preferably the membrane also contains a covalently bound (this time not necessarily cross-linked, but preferably so) mediator, e.g. methyl methacrylate. The mediator may be present in a proportion of 1 to 10% by weight (preferably 4 to 8% by weight) with respect to the membrane. A mediator modifies the calcium selectivity in the presence of other divalent cations, and/or modifies the divalent-ion-selectivity in the presence of monovalent cations. The latter feature is significant especially in clinical measurements, where sodium (typically in decimolar concentration in body fluids) rather masks the calcium response of electrodes without a mediator at calcium concentrations below about centimolar.

The invention will now be described by way of example with reference to the accompanying drawing, which illustrates an ion-selective electrode according to the invention.

EXAMPLE 1

A screened cable 1 leads to a silver/silver chloride electrode 2 in a decimolar aqueous solution 3 of calcium chloride contained in a glass tube 4 with a polyvinyl chloride tubular extension 5 closed by an ion-selective membrane 6.

The membrane 6 is made as follows: Tetrahydrofuran was freshly distilled from $LiAlH_4$ to dry it and to remove stabilisers. Triallyl phosphate was used as received. An initiator, α,α-azobisisobutyronitrile, was recrystallised from methanol. The polymer used was Cariflex SBS 1101 (trade mark of Shell Chemicals, London) which was purified by dissolving in the tetrahydrofuran and reprecipitating into cold, well-stirred methanol. Gel permeation chromatography showed the number average relative molecular mass (Mn) as $9.8 \times 10^4$ g.mole$^{-1}$ with 70% styrene-butadiene-styrene triblock poly(styrene-b-butadiene), 26% styrene-butadiene diblock and 4% homopolystyrene content. The polydispersity (Mw/Mn) was 1.51; nuclear magnetic resonance spectroscopy (n.m.r.) at 100 MHz indicated 27% by weight polystyrene in the polymer, hence 73% by weight as polybutadiene. 300 MHz nuclear magnetic resonance spectroscopy showed the butadiene units to be of 90% 1,4- and 10%, 1,2- configuration.

Reprecipitated styrene-butadiene-styrene (4 g) was dispersed in 40 ml of the tetrahydrofuran and allowed to dissolve overnight. Then, 4.4% by weight of triallyl phosphate and 2.5% by weight of α,α-azobisisobutyronitrile as initiator were added with mixing. The mixture was then poured into a glass ring (100 mm internal diameter) pressed by a heavy weight on to a cellophane (transparent viscose material) sheet which rested on a glass plate. A front-silvered mirror was arranged to reflect normally on to the plate. The mixture is cured by free radical initiation by shining ultraviolet radiation (suitably a flux of $1.6 \times 10^8$ candela m$^{-2}$) with the aid of the mirror. The mixture was fully cured after 6 hours, this varying with solvent volatility, forming a strong clear membrane about 1 mm in thickness of the triblock copolymer with cross-linked trialkyl phosphate derived from the original triallyl phosphate. Membranes made in this way were removed from the cellophane and portions hydrolysed for 5 hours each in 5% KOH in methanol to give the master membrane. The hydrolysis converts the trialkyl phosphate into the desired more stable and active exchanger, dialkyl phosphate. The membrane could be made by pressing rather than casting.

A disc, 10 mm in diameter, was cut from the master membrane and stuck to the end of clear, plasticised PVC tubing (to form the extension 5) using a cyanoacrylate adhesive. Calcium chloride solution (0.1 M) saturated with silver chloride was used as the internal reference standard solution 3. The disc was soaked overnight in 10$^{-2}$ M Ca$^{2+}$ solution in order to convert the K$^+$ form of the sensor (the dialkyl phosphate) to the Ca$^{2+}$ form. The necessary soaking time depends on the degree of cross-linking, but 12 hours (conveniently overnight) is usually enough.

A poly(styrene-b-butadiene) triblock elastomer is preferred because it contains the necessary C=C unsaturation for cross-linking; has mechanical behavior similar to natural rubber volcanizates, without requiring cross-linking; can be dissolved in solvents; and is easy to process. In order to incorporate the phosphate sensor groups, the unsaturated C=C bonds are cross-linked by a free-radical initiated addition mechanism using triallyl phosphate.

In order to obtain the dialkylphosphate sensor unit, it is necessary to hydrolyse the trialkylphosphate system with alkali. The stability of the resonance-stabilised dialkylphosphate salt is such that further hydrolysis to remove other alkyl groups is very difficult and will not proceed under the conditions used. This leaves the dialkylphosphate group covalently bound to the polymeric membrane. Strong alkaline hydrolysis results in attack on the polymer itself, presumably at the residual unsaturation, and, at approximately 25% by weight aqueous sodium hydroxide, the polymeric material breaks down completely.

Using mild aqueous alkaline conditions for hydrolysis gave membranes which showed near-Nernstian slopes but with short life-times. Those with longer life-times had significantly sub-Nernstian calibration slopes. Aqueous hydrolysis furthermore produced membranes which were more soluble in tetrahydrofuran than the unhydrolysed membranes, presumably due to further attack on the polymer structure in addition to hydrolysis of phosphate groups, and therefore is less preferred, although possible.

Hydrolysis using 5% methanolic potassium hydroxide proceeded smoothly resulting in an insoluble membrane with a Nernstian response and an extended lifetime.

Excessive initiator reduced the response and clarity of the membrane, while an excessive proportion of sensor groups resulted in an oily non-functional membrane. Insufficient of these components resulted in poorly cross-linked membranes.

The membrane according to the above example displayed a linear response to Ca$^{2+}$ concentrations from below 10$^{-6}$ M up to 10$^{-2}$ M, at +30 mV per decade at 25° C., with reproducibility within about 1 mV, and drift of about 1 mV/day. The static response time was about 5 seconds down to 10$^{-4}$ M, and about 15 seconds at 10$^{-6}$ M. Dynamic response times to suddenly-effected tenfold changes in calcium concentration were mostly about 1 second, increasing to about 5 seconds at 10$^{-6}$ M.

The selectivity shown by the ion-selective electrode is in the order Ca$^{2+}$ > Ba$^{2+}$ > Mg$^{2+}$ > M$^+$. Potentiometric selectivity coefficients at the 10$^{-3}$ M interferent level electrode are: $k_{CaBa}^{pot} = 0.8$ and $k_{CaMg}^{pot} = 0.3$. The electrode could be used over the pH range 4–10. Interference from monovalent ions is much less than for divalent ions which makes possible the hydrolysis in KOH or NaOH, with the exchange sites created as the K$^+$ or Na$^+$ form, followed by the conditioning in concentrated (0.1 M) Ca$^{2+}$ solution allowing replacement to the required calcium form. At Na$^+$ concentrations of 10$^{-3}$ M, and even 10$^{-2}$ M, calcium response is reasonable.

The life-time of the electrode, stored in 10$^{-2}$ M Ca$^{2+}$ solution and calibrated at least once a week, is in excess of 6 months.

This electrode may be used for water-hardness measurement, where divalent cations other than calcium have much the same 'hardening' effect as calcium and are present in a smaller concentration, and where monovalent cations are relatively rare. Similar conditions obtain in coking plant effluent, where this electrode may therefore also be used.

EXAMPLE 2

In this Example a membrane has its physical and electrochemical properties modified by the inclusion of a mediator such as methylmethacrylate. The preparation is as follows:

Reprecipitated styrene-butadiene-styrene (4 g) was dispersed in 40 cm$^3$ of tetrahydrofuran and left to dissolve overnight. Then 4.5% by weight of triallyl phosphate, 5% by weight of redistilled methyl methacrylate and 2.5% by weight of α,α-azobisisobutyronitrile (as initiator) were added with mixing. This mixture was cast and cured as in Example 1. The mixture was fully cured after six hours, this varying with solvent volatility, forming a membrane, about 1 mm in thickness, of the triblock copolymer with cross-linked triallyl phosphate derived from the original triallyl phosphate and covalently bound methyl methacrylate units derived from the redistilled monomeric methyl methacrylate. The membrane was slightly opaque and less elastic than that derived from the use of triallyl phosphate as sole cross-linking agent. The resulting membrane was hydrolysed for 1 hour in 5% KOH in methanol to give the master membrane from which ion-selective electrodes were fabricated as in Example 1.

We claim:

1. An ion-selective electrode comprising a standard solution of the ion and, retaining the solution, a membrane comprising an unsaturated organic polymer having sensor groups covalently bonded to said polymer, characterized in that the unsaturated organic polymer is cross-linked at least in part through a covalently-bonded sensor group of the formula

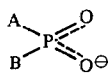

where A and B are unsaturated moieties cross-linking the polymer, whereby the electrode is calcium-selective.

2. An ion-selective electrode according to claim 1, characterised in that the membrane comprises an unsaturated linear polymer.

3. An ion-selective electrode according to claim 2, characterised in that the unsaturated linear polymer is a styrene-butadiene-styrene triblock copolymer.

4. An ion-selective electrode according to claim 1, characterised in that the membrane displays elastomeric properties.

5. An ion-selective electrode according to claim 1, characterised in that the membrane contains a covalently bound mediator.

6. An ion-selective electrode according to claim 5, characterised in that the mediator is cross-linked to the membrane.

7. An ion-selective electrode according to claim 5, characterised in that the mediator is methyl methacrylate.

8. An ion-selective electrode according to claim 1, characterised in that the sensor group is an organophosphate or an organophosphonate.

9. An ion-selective electrode according to claim 9, characterised in that the sensor group is dialkyl phosphate.

10. A method of making the ion-selective electrode of claim 9, characterised in that the dialkyl phosphate is made directly from a cross-linking reaction of diallyl phosphoric acid with the membrane yielding dialkyl phosphate.

11. A method of making the ion-selective electrode of claim 9, characterized in that the dialkyl phosphate is made indirectly from a cross-linking reaction of a compound selected from the group consisting of triallyl phosphate, tri(ω-undecenyl)phosphate and diallyl phenylphosphonate with the membrane yielding trialkyl phosphate.

12. A method according to claim 11, characterised in that the cross-linking reaction is free-radical initiated.

13. A method according to claim 12, characterised in that α,α-azobisisobutyronitrile is present as a free-radical initiator.

14. A method according to claim 12, characterised in that the proportion of free-radical initiator is 1 to 5% by weight with respect to the membrane.

15. A method according to claim 14, characterised in that the said proportion is 2 to 3% by weight.

16. A method according to claim 12, characterised in that the free radicals are generated by ultra-violet irradiation.

17. A method according to claim 11, characterised in that the cross-linking reaction is followed by hydrolysis converting the trialkyl phosphate to dialkyl phosphate.

18. A method according to claim 17, characterised in that the hydrolysis lasts at least 1 hour.

19. A method according to claim 18, characterised in that the hydrolysis lasts at least 3 hours.

20. A method according to claim 19, characterised in that the hydrolysis lasts at least 4 hours.

21. A method according to claim 17, characterised in that the hydrolysis lasts up to 20 hours.

22. A method according to claim 21, characterised in that the hydrolysis lasts up to 10 hours.

23. A method according to claim 18, characterised in that the hydrolysis is by aqueous alkali in a concentration of up to 20% by weight.

24. A method according to claim 17, characterised in that the hydrolysis is by up to 8% by weight alkali in alcohol.

25. A method according to claim 11, characterised in that the phosphate according to the cross-linking reaction is present in a proportion of 0.3 to 10% by weight with respect to the membrane.

26. A method according to claim 25, wherein the said proportion is 4 to 6% by weight.

* * * * *